United States Patent
Patell

(10) Patent No.: US 7,994,406 B2
(45) Date of Patent: Aug. 9, 2011

(54) RICE CONFERRING RESISTANCE TO ENVIRONMENTAL STRESS BY TARGETING MNSOD TO THE CHLOROPLAST

(75) Inventor: Villoo Morawala Patell, Bangalore (IN)

(73) Assignee: Avestha Gengraine Technologies Pvt. Ltd., Bangalore (IN)

( * ) Notice: Subject to any disclaimer, the term of this patent is extended or adjusted under 35 U.S.C. 154(b) by 0 days.

(21) Appl. No.: 10/552,887

(22) PCT Filed: Dec. 9, 2002

(86) PCT No.: PCT/IB02/05253
§ 371 (c)(1), (2), (4) Date: Oct. 12, 2005

(87) PCT Pub. No.: WO2004/053136
PCT Pub. Date: Jun. 24, 2004

(65) Prior Publication Data
US 2007/0006349 A1    Jan. 4, 2007

(51) Int. Cl.
*A01H 5/00* (2006.01)
*C12N 15/82* (2006.01)

(52) U.S. Cl. .................................................. 800/320.2

(58) Field of Classification Search ................. None
See application file for complete search history.

(56) References Cited

U.S. PATENT DOCUMENTS
5,538,878 A    7/1996    Thomas et al.

FOREIGN PATENT DOCUMENTS
EP    0 356 061        2/1990
EP    0359 617 A2 *    3/1990
EP    0359617          3/1990

OTHER PUBLICATIONS

Tanaka et al. (Plant Science, 148:131-138, 1999).*
Nayak et al. Transgenic elite indica rice plants expressing CryIAc delta-endotoxin of Bacillus thuringiensis are resistant against yellow stem borer (Scirpophaga incertulas). Proc Natl Acad Sci U S A. Mar 18, 1997;94(6):2111-6.*
Verdaguer et al. Isolation and expression in transgenic tobacco and rice plants, of the cassava vein mosaic virus (CVMV) promoter. Plant Mol Biol. Sep. 1996;31(6):1129-39.*
Davuluri et al. Oxidative stress management-targeting MnSOD to the chloroplast. Meeting Abstract. Plant Biology (Rockville), (1999) vol. 1999, pp. 103. print. Meeting Info.: Annual Meeting of the American Society of Plant Physiologists. Baltimore, Maryland, USA. Jul. 24-28, 1999. American Society of Plant Physiologists (ASPP).*
Li et al. An improved Rice transformation system using the biolistic method. Plant Cell Rep. 1993. 12: 250-255.*
Van Camp et al., "Elevated Levels of Superoxide Dismutase Protect Transgenic Plants Against Ozone Damage" Bio/Technology vol. 12, pp. 165-168 Feb. 12, 1994.
Yu et al., "Waterlogging Influences Plant Growth and Activities of Superoxide Dismutases in Narrow-leafed Lupin and Transgenic Tobacco Plants" Journal of Plant Physiology pp. 431-438 1999.
Rao et al., "Oxidative Stress Management-Targeting MnSOD to the Chloroplast" American Society of Plant Biologists vol. 1999, pp. 103 XP001208344.
Bowler et al., "Manganese Superoxide Dismutase Can Reduce Cellular Damage Medicated by Oxygen Radicals in Transgenic Plants" The EMBO Journal vol. 10, No. 7, pp. 1723-1732 1991.
International Search Report for International Application No. PCT/IB02/05253 dated Jul. 28, 2003.
Yu et al. Increased Tolerance to Mn Deficiency to Transgenic Tobacco Overproducing Superoxide Dismutase. Ann. Bot. 1999, vol. 84, pp. 543-547, see whole document.
Slooten et al. Factors Affecting the Enhancement of Oxidative Stress Tolerance in Transgenic Tobacco Overexpressing Manganese Superoxide Dismutase in the Chloroplasts. Plant Physiol. 1995, vol. 107, pp. 737-750, see whole document.
McKersie et al. Superoxide Dismutase Enhances Tolerance of Freezing Stress in Trahsgenic Alfalfa (Medicago sativa L.) Plant Physiol. 1993, vol. 103, pp. 1155-1163, see whole document.
Lambe et al. Differential long-term expression and methylation of the hygromycin phosphotransferase (hph) and B-glucuronidase (GUS) genes in transfenic pearl millet.
Van Breusegem et al. Effects of Overproduction of Tobacco MnSOD in Maize Chloroplasts on Foliar Tolerance to Cold and Oxidative Stress. J. Exp. Bot. Jan. 1999, vol. 50, No. 330, pp. 71-78, see whole document.
Tanaka et al. Salt Tolerance of Transgenic Rice Overexpressing Yeast Mitochondrial MnSOD in Chloroplasts. Plant Sci. 1999, vol. 1487, pp. 131-138, see whole document.

* cited by examiner

Primary Examiner — Cynthia Collins
(74) Attorney, Agent, or Firm — Hamre, Schumann, Mueller & Larson, P.C.

(57) ABSTRACT

The present invention relates to the induction of the endogenous MnSOD expression in the chloroplast which scavenges reactive oxygen species in the plant cells and provides the means of cultivating crops in areas where it would not otherwise grow normally on account of environmental stress conditions inclusive of high and low temperatures, drought and ultra violet light, and resistance to herbicides so as to increase yield and improve crop quality.

2 Claims, 6 Drawing Sheets

Immunofluorescence

RICE CONFERRING RESISTANCE TO ENVIRONMENTAL STRESS BY TARGETING MNSOD TO THE CHLOROPLAST

FIELD OF THE INVENTION

The present invention relates to the overexpression of MnSOD in the Chloroplast which is the site of production of reactive oxygen species and provides the means and wherewithal of cultivating crops in areas where it would not otherwise grow normally on account of environmental stress conditions inclusive of high and low temperatures, drought and ultra violet light, is resistant to herbicides thereby resulting in an increase in yield and also improved crop quality.

BACKGROUND

Environmental stress in a broad sense is a restriction placed on living organisms by nature. The definition of environmental stress in plant science is a set of physical and chemical factors affecting the environment consequently disturbing plant growth. This stress could occur due to variant temperatures be it high or low, insufficient water supply, ultraviolet radiation and emission of pollutant gases. The study of environmental stress in plant life is significant on account of the fact that it world over agricultural productivity has been greatly restricted by it and the need to withstand this kind of environmental stress is a prerequisite when studying plant life.

Under stressful conditions, the stress factor or toxic molecules derived from the stress factor attack the more sensitive molecules i.e. the primary targets in cells to impair their functions. Cells are protected by the endogenous molecular systems which mitigate the stress. The damaged targets either by having them repaired or replaced are recovered via de novo biosynthesis. When the damage caused by stress to the primary targets is very intense, the cell cannot get over the damage and the metabolic function(s) operated by the target molecules are distorted. If the repair system in respect of the damaged molecules or the energy supply system is impaired, viz, the entire cellular metabolism disintegrates allowing for the propagation of damages, then there is a cascade of events leading to cell death.

Cells have the capability of surviving stressful conditions by sensing stress and adjusting their gene expression pattern to establish new metabolism which adapt to the stress. This adaptive response is known as acclimation and it takes place from a few hours to several days in which time cells take on the stress by making use of pre existing protection systems until the new metabolism is established. The destiny of the cell is determined by the degree of available protection and the intensity and duration of the stress. The investigation of the cellular response in the early stages of environmental stress reveal the endogenous and exogenous factors that determine the stress tolerance of the plant.

The production of reactive oxygen species in cells is an inevitable restriction on aerobic life and use is made of the oxidative atmosphere for yielding energy at a high efficiency. In so far as the metabolism under non stressful conditions is concerned, reactive oxygen species is always produced. The reactive oxygen species is produced in the cells for biosynthesis, cell defence, intra and intercellular signalling. Hence, reactive species of oxygen is both, indispensable as well as toxic to life.

It has been observed that reactive oxygen species plays a crucial role in the impairment of cellular functions due to environmental stress viz, increase in the productive of reactive oxygen species and production of oxidised target molecules under stress, decrease in the antioxidant levels or contents under stress, increased expression of the genes for antioxidative functions by stress, positive co-relation between the scavenging capacity for reactive oxygen species and tolerance towards stress, cross tolerance between oxidative stress and other stress.

Oxidative damage caused by reactive oxygen species can be induced by two principal mechanisms viz, an enhanced production of reactive oxygen species or by an inhibition of the scavenging systems for them. The damage proliferates production of a highly reactive hydroxyl radical and the subsequent reactions like bleaching of pigments and accumulation of oxidised lipids are apparent, these being the final symptoms of oxidative damage observed in dying cells.

Superoxide is a commonly encountered mediate of oxygen reduction. It is extremely toxic to cells since it attacks unsaturated fatty acid components of membrane lipids thereby damaging the membrane structure. Aerobic cells detoxify super oxide by the action of super oxide dismutases, metal containing enzymes that convert the superoxide radical into hydrogen peroxide and molecular oxygen. The hydrogen peroxide later converted by catalase into water and molecular oxygen.

There are three types of super oxide dismutase (SOD), copper/zinc containing SOD(CuZnSOD), manganese containing SOD (MnSOD) and iron containing SOD (FeSOD). In prokaryotic organisms MnSOD is inducible under conditions of high oxygen concentration and by $O_2$.

Reactive oxygen species is produced in almost every cell compartment in instances of normal metabolism (Halliwell & Gutteridge, 1989). The chloroplast containing pigments at high concentrations and evolving $0_2$ under light is a major source of reactive species in plant cells under illumination (Asada & Takashahi, 1987). The chloroplast and the leaf tissue is regarded as a primary site of stress induced damage in plants under light. However there are numerous cases wherein the stimuli arise from extrachloroplastic sites, e.g., the ozone, which, penetrates into the leaf tissue and interacts with apoplastic components on account of which the apoplastic antioxidant capacity assumes significance. Biotic stress like bacterial infection and grazing arises from the periphery of the cells. In the case of water stress like drought and high saline content in the soil, stress stimuli are sensed primarily by roots as well as the leaves.

In an instance where the chlorophyll (Chl) molecule at the photochemical reaction centre in the thylakoid membranes absorbs light energy, a high potential oxidative power i.e. a positive charge and a low potential reducing power, a negative charge is generated. On the oxidative side of the photosystem II (PSII) the oxidative terminus of the photosynthetic electron transport chain, water is oxidised to $O_2$. On the reducing side of photosystem I (PSI) the opposite terminus, the iron-sulphur protein ferredoxin (Fd) is reduced. The reduced Fd provides electrons for $CO_2$ fixation and other reactions in the chloroplast. There are two potential production sites for reactive oxygen species, the reducing side of PSI and PSII.

The redox potential of the FeS centres at the terminus of PSI, $\ni 0.4$ is low enough to reduce $0_2$ univalently to produce superoxide radical ($0_2\ni$). $0_2$+PSI reduced$\rightarrow 0_2\ni$+PSI (oxidised). The photoreduction of $O_2$ to $O_2\ni$ by PSI (Asada & Kiso, 1973b) inevitably occur and uses 10-20% of the photosynthetic electron flux even under conditions where $C0_2$ supply saturates (Asada & Takahashi, 1987). $O_2\ni$ is disproportionate to $H202$ and $O_2$ via catalysis by superoxide dismutase (SOD) which is contained in the stroma (Asada et al., 1973).

$2O_2\ni+2H+\rightarrow H_2O_2+O_2$: These reactions account for most of the photoproduction of H2O2 in chloroplast (Mehler reaction; Mehler, 1951). $H_2O_2$ is produced via non-enzymic reduction of $O_2\ni$ with ascorbate (AsA) or glutathione (GSH).

$O_2\ni+AH\rightarrow H_2O_2+A\forall$, where AH and $A\forall$ represent either AsA or GSH and its radical, respectively. Under normal physiological conditions this mechanism is neglected since the produced $O_2\ni$ is immediately disprorportioned with SOD, which resides near the production site of $O_2\ni$ (Ogawa et al., 1995).

O2 photoproduced from $H_2O$ in PSI II is finally reduced to $H_2O$ in PSI, with catalysis by SOD and APX, to form a cycle of electron flow (water-water cycle; Asada et. Al, 1998). With regard to the produced reactive oxygen species scavenged in situ by the enzymes of the water cycle, the photoreduction of $O_2$ to $O_2\ni$ is not detrimental but indispensable in preventing photoinhibition of chloroplast by acting as a safety valve that dissipates excessive excitation energy as heat (Schreiber & Neubauer, 1980, Neubauer & Yamamoto, 1922, Osmond & Grace, 1995, Laisk & Edwards, 1998). Even at $1.1^{o/o}$, $CO_2$ that saturates photoreduction of $CO_2$ in chloroplast, the electron flow to $O_2$ prevents photoinhibition despite producing $O_2\ni$ (Park et al., 1996). This efficient scavenging of $O_2\ni$ and $H_2O_2$ is ensured by high molecular activities and intraorganellar microlocalisation of the water-water cycle enzymes (Asada et al., 1998). The chloroplastic flavoenzyme monodehydroascorbate reductase has been suggested to regulate the photoproduction rate of $O_2\ni$ at PSI (Miyake et al., 1998).

$H_2O_2$ is also produced outside the chloroplast not only via the disproportionation of $O_2\ni$ but also via the divalent reduction of $O_2$ catalysed by various oxidases which catalyse divalent oxidation. H2O2 if provided with reductants and an appropriate catalyst, e.g. transition metal ions, quinones and Fd (Jacob & Heber, 1996), is reduced to form a highly toxic hydroxyl radical (HO$\psi$) (Heber-Weiss reaction). $H_2O_2+AH\rightarrow HO\psi+OH\ni+A$. AsA, GSH and $O2\ni$ can be reductants for this reaction. As catalysts the FeS centres in PSI reaction complex (Sonoike, 1996b) and in Fd (Jacob & Heber, 1996) might produce HO$\psi$ in situ. Transition metal ions e.g. Fe, Cu and Mn, if released from metalloenzymes for some reasons are also effective catalysts. Cd from the environment also catalyses the Haber-Weiss reaction. HO$\psi$ production is implied in the oxidative stress caused by excess Fe in tobacco (Kampfenkel et al., 1995). HO$\psi$ can also be detected on the donor side of PS II which is impaired by UV-B (Hideg & Vass, 1996) although the source and the reaction to produce this radical is not yet known, as of now. HO$\psi$ is highly oxidative (redox potential of HO$\psi$/$H_2O$; +2.3 V) and oxidises organic molecules at the constant rate of 109 MD sD1 (Halliwell & Gutteridge, 1989) and is toxic.

At the other end of the electron transport chain, at the time when the charges separated at the Ch1 dimer at the reaction centre recombine, the triplet state of Ch1 (3Ch1) is formed and it reacts rapidly with ground state oxygen ($3O_2$) to form a singlet oxygen ($1O_2$). $3Ch1+3O_2\rightarrow 1$ $Ch1+1O2$. $1O2$ is also produced via a similar photodynamic reaction with heme groups in proteins and with flavins through various reactions from $O_2D$ and $H_2O_2$ (Halliwell & Gutteridge, 1989). In PSI II reaction centre, $1O_2$ is produced when the primary acceptor quinone QA is fully reduced (Vass & Styring, 1993). The photoproduction of 1O2 in PSI II has been observed in vitro (Macpherson et al., 1993) and in vivo (Hideg et al., 1998). $1O_2$ is highly reactive with organic molecules and consequently, highly toxic as well. The oxidative potential generated in the PSII reaction centre required for the oxidation of water to oxygen is potentially toxic to the PSII complex itself and damages it as a probable event (Anderson et al., 1998). The oxidant is harnessed with a charge accumulation mechanism of the Mn cluster of water oxidase (Kok et al., 1970) so as not to release the possibly generated intermediates of water oxidation, HO$\psi$, H2O2 and O2D. When water oxidase is destroyed on account of some reason or the other, such as UV-B or heat, the photogenerated oxidative power as P680+ or Tyrz+, may, oxidise the surrounding protein matrix or neighbouring molecules to inactivate PSII complex (donor-side-induced photoinhibition; Blubaugh et al., 1991, Aro et al., 1993). Further, reactive oxygen species that can be produced through photooxidation of water, may be released (Ananyev et al., 1992, Fine & Frasch, 1992, Hideg et al., 1994).

In additional chloroplastic compartments, the major production reaction for reactive oxygen species are not only the univalent reduction of $O_2$ to O2D but the divalent reduction of $O_2$ to $H_2O_2$. Peroxisomes contain divalent reaction oxidases and produce $H_2O_2$ in association with oxidative metabolisms like photorespiration and -oxidation of lipids. In C3 plants a substantial amount of $H_2O_2$ is produced and accompanies the photorespiration through the peroxisomal glycolate oxidase.

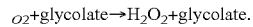
$o_2$+glycolate→$H_2O_2$+glycolate.

Acyl-CoA oxidase in peroxidase catalyses divalent oxidation of acyl-CoA to trans-2, 3-dehydroacyl-CoA by $O_2$ in the beta-oxidation of lipids, producing $H_2O_2$. $O_2D$ is produced in mitochondria. In mammalian mitochondria, $O_2D$ production due to electron leakage from the electron transport to $O_2$ accounts for 1-2% of total electron flux through the chain (Chance et al., 1979) and is increased several fold by the inhibitors of electron transport, uncouplers and other agents to disrupt mitochondrial functions (Richter & Schweizer, 1997). The production of $O_2D$ in submitochondrial particles from pea leaves has been demonstrated (Hernandez et al., 1993). Assuming that mitochondria is a major production site of $O_2D$ in non photosynthetic cells, it has not yet been elucidated as to whether the production of $O_2D$ in mitochondria has a physiologically positive significance as that in the chloroplast. $O_2D$ is also produced in peroxisome and plasma membrane. In plant peroxisome, $O_2D$ is produced via xanthine oxidase and at least three distinct NAD (P)H oxidases (del Rio, 1998). Peroxisomal $O_2D$ production is increased during senescence and the reactive oxygen species derived from it, decompose cellular components (Brennan & Frenkel, 1977, del Rio et al., 1998). Participation in the production of $O_2D$ of a mammalian like NADPH-oxidase on the plasma membrane in plant cells has been established upon extracellular stimuli (Auh & Murphy, 1995, Allan & Fluhr, 1997) and during lignification (Ogawa et al., 1997).

Reactive oxygen species have their respective molecular properties and reactivities with biomolecules with scavenging mechanisms for both. $O_2D$ is generally known as a relatively stable or unreactive molecule among the reactive oxygen species. However the protonated form $HO_2$ (pKa=4.8) is a much higher reactive. HO2 can initiate lipid peroxidation but not $O_2D$. Moreover $HO_2$ can pass across lipid bilayers but not O2D. In an aqueous solution, $O_2D$ spontaneously disproportionates to form $H_2O_2$ and $O_2$.

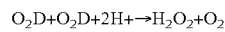
$O_2D+O_2D+2H+\rightarrow H_2O_2+O_2$

At a lower pH, the following reactions may occur:

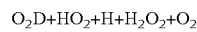
$O_2D+HO_2+H+H_2O_2+O_2$

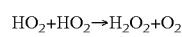
$HO_2+HO_2\rightarrow H_2O_2+O_2$

The second order rate constants for these reactions are <0.35 MD1 sD1, 1.02×107 MD1 sD1 and 8.60×105 MD1 sD1. Since the reaction constant is the largest apparent second order rate constant for the disproportionation of $O_2D$, 5-105 MD1 sD1 at pH 7.0, thus decreases by 10 fold per each pH unit increase in the range over pH 5 (Bielski, 1978). $O_2D$ is a reductant of the transition metal ions in the Haber-Weiss reaction to produce $HO\psi$ from $H_2O_2$. $O_2D$ also propagates radical chain reaction especially in the presence of quinone. When quniones are univalently reduced to semiquinones ($QH\psi$) with quinone reductases which abundantly occur in plant cells, parts of the $QH\psi$ reduces dioxygen to produce $O_2D$, which oxidises the quinols that have been produced via the disproportination of $QH\psi$ to reproduce $QH\psi$. This chain reaction is effectively terminated by SOD (Cadenas et al., 1992).

$O_2D$ is highly reactive with reduced sulfur compounds like thiols and FeS cluster. $O_2D$ oxidises thiols to the thiyl radicals at diffusion controlled rates (Asada & Kanematsu, 1976). The resulting thiyl radicals initiate radical chain reaction. $O_2D$ also oxidises the 4 Fe-4S) cluster of aconitase in mammalian mitochondria or in bacteria at the order of 106-107 MD1 sD1 to the inactive (3Fe-4S) form (Radi et al., 1998). The Fe2+ ion released as a consequence is a potent catalyst for Haber-Weiss reaction. In plant cells the major SOD isozymes are located in chloroplasts (MnSOD). The occurrence of CuZnSOD in the apoplast and nucleus has been confirmed by immunoelectron microscopy (Ogawa et al., 1995). The occurrence of SOD implies the in situ production of $O_2D$. CuZnSOD and FeSOD are sensitive to $H_2O_2$. These SODS are the potential targets if the $H_2O_2$ scavenging systems do not operate properly.

$H_2O_2$ is a neutral, non radical molecule below pH 10 and can diffuse across biomembranes like water. The function of $H_2O_2$ as a stress signal (Doke, 1997) is partly based on its intra and inter cellular diffusability. $H_2O_2$ is a relatively weak oxidant, the oxidative potential of $H_2O_2/H_2O$ pair is +320 mV. However, metalloenzymes are in general sensitive targets of $H_2O_2$. Heme proteins can catalyse the Haber-Weiss reaction and can be degraded by the resulting $HO\psi$ (Puppo & Halliwell, 1998). Chloroplastic APX isozymes are inactivated by $H_2O_2$ in the absence of electron donors (Hossain & Asada, 1984) since compound I is irreversibly oxidised by H202 (Miyake & Asada, 1996). CuZnSOD is inactivated by $H_2O_2$ (Bray et al., 1974) through the reduction of Cu2+ ion at the reaction centre to Cu+ and the subsequent production of $HO\psi$ (Hodgson & Fridovich, 1975). CuZnSOD in isolated chloroplast of wheat leaves are inactivated by insufficient light probably due to photoproduced $H_2O_2$ (Casano et al., 1997). FeSOD is also inactivated by $H_2O_2$ (Beyer & Fridovich, 1987). The inactivation of these enzymes have been observed in vitro at the _M to sub-mm range of $H_2O_2$, which can be reached in vivo as well if the $H_2O_2$ scavenging systems do not operate effectively. $H_2O$ oxidises thiols to the sulfenic acids which react with thiols to form disulfides. The reaction between $H_2O_2$ and cysteine is slow (the apparent second order rate constant, 1MD1, sD1) but on the surface of the proteins the reaction may be largely accelerated by the presence of basic residue like Lys and Arg which could be the neighbouring thiol groups (Armstrong & Buchanan, 1978). $H_2O_2$ at micromolar concentrations in darkness inhibit C02 fixation in the chloroplast by 50% in 10 min (Kaiser, 1979) due to the oxidation of the active site thiols to the disulfide in the Calvin cycle enzymes; fructose-1; biphosphatase, NADP-glyceraldehydes-3-phosphate dehydrogenase and ribulose-5 phosphate kinase. The activities of these inhibited enzymes are recovered by the reduction with reduced thioredoxin reversibly (Wolosiuk & Buchanan, 1977). However, if cessation of $CO_2$ continues under light, it will lead to excess light energy wherein the production of reactive oxygen species increases.

$H_2O_2$ is scavenged by two types of enzymes, catalase and peroxidase. The former scavenges H202 through the disproportination of $H_2O_2$ to $O_2$ and $H_2O$ corresponding to a turnover rate of about 107 minD1. (Scandalios et al., 1997). $2H_2O_2 \rightarrow O_2 + 2H_2O$. Plants have several catalase isozymes, which are expressed in the regulated stage and tissue (Scandalios et al., 1997). Catalase is localised mainly in peroxisomes and responsible for scavenging the $H_2O_2$ produced in photorespiration and beta-oxidation of lipids. Catalase is a key antioxidant enzyme, a tetrameric heme containing enyme found in nearly all the aerobic organisms which converts hydrogen peroxide into water and molecular oxygen in plants and are primarily located in peroxisomes. Plant catalases are involved in the detoxification of active oxygen species which are generated during the course of photorespiration, the beta-oxidation of fatty acids or different environmental stresses (Scandalios, 1990).

It has been shown that induction of superoxide dismutase activity in plant cells has been correlated with development of increased tolerance to a variety of chemical compounds and physical stress. Environmental stress is known to decrease crop activity according to the severity and type of stress. Enhancing tolerance of crop plants to adverse effects imposed by non optimal growing conditions for improvement of crop management. There is hence, a substantial interest in the ability to increase the concentration of super oxide dismutase in a plant cell so as to provide for a plant which has increased tolerance to environmental stress.

SUMMARY OF THE INVENTION

The present invention necessitated a comparative study of the MnSOD gene expression at mRNA level during the abiotic stress in the seedlings of contrasting *Indica* Rice varieties, IR64 and RASI, and offers a simple yet powerful tool to monitor alterations in the gene expression and further, has proved the dramatic induction of MnSOD during stress conditions. Further, the superoxide radical triggers a specific molecule in each sub cellular compartment, which is capable of acting as a signal to induce nuclear gene encoding for the particular superoxide dismutase associated with that compartment.

In the present invention, we have generated transgenic *Japonica* rice plants by co-transforming three week old scutellum callus using particle accelerator Biolistic PDS-1000/He with the plasmid, pGV2. The plasmid pGV2 carried the MnSOD cDNA (Bowler et al, 1989), cloned downstream of CaMV promoter and the chloroplast targeting peptide followed by the NOS terminator. The pILTAB222 carried the hygromycin B phosphotransferase downstream of 35S CaMV promoter, followed by the NOS terminator.

DESCRIPTION OF THE INVENTION

Figure 1A:
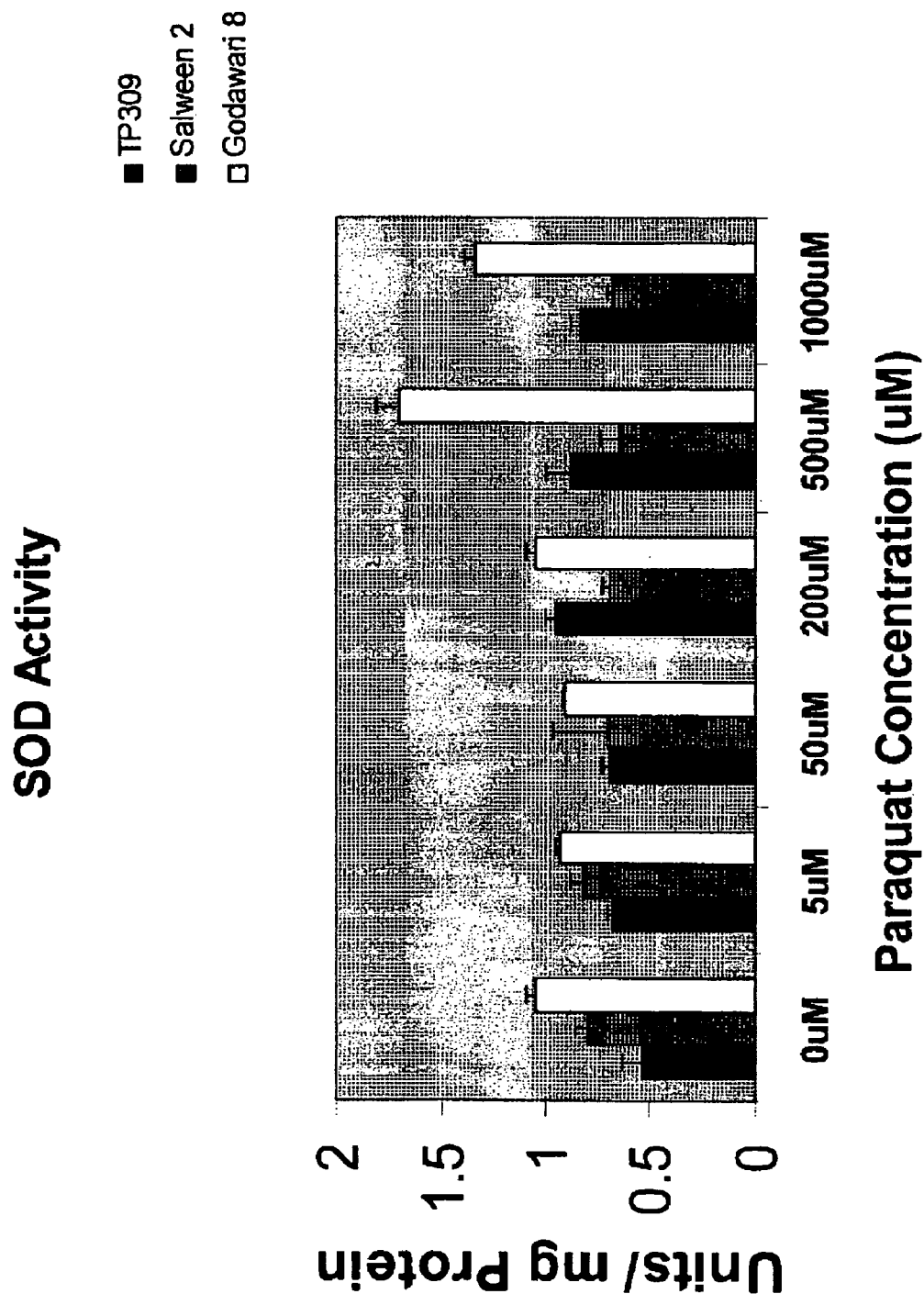
FIG. 1a shows levels of SOD activity in TP309, Salween 2 and Godawari 8.

Exposure of plants to stress conditions results in an inhibition of photosynthesis. The effects of oxygen toxicity and photoinhibition are strongly directed towards photosynthesis. Plants engineered to produce increased levels of SOD activity in response to environmental stress find use in being able to grow under conditions which inhibit growth of the parental strain, in particular conditions which increase plant super oxide to growth inhibitory levels. Examples of such conditions include salinity, drought and elevated metal concentration of the rhizosphere.

In eukaryotes, MnSOD, is a nuclear encoded protein which scavenges superoxide radicals in the mitochondrial matrix. The superoxide radicals have been ubiquitously generated in biological oxidation in all compartments of the cell. The increased production of superoxide radical is associated with a number of physiological disorders in plants. By targeting the MnSOD enzyme to the chloroplast, where the generation of superoxide is high during stress conditions, the capacity to scavenge any radical that is produced, can be increased. The chloroplast transit peptide of the small sub unit of Rubisco (ssTP) has been successfully used in both, monocotyledonous and dicotyledonous plants to target different transgenic non-plastid proteins (Cashmore et al, 1983).

The usefulness of the invention lies in the fact that it relates particularly to the use of the MnSOD gene for the protection of the plant against naturally occurring stress conditions which are not normally within the control of a farmer and as a result, the invention provides the means for growing crops in geographical areas in which they could not heretofore be grown with reasonable yields due to such naturally occurring stress conditions, including herbicide resistance, high and low temperatures, Ultra Violet light and drought.

The transgenic plant is resistant or tolerant to stress conditions, particularly naturally occurring stress conditions which produce highly reactive oxygen species in one or more compartments of the plant cells, thereby increasing the potential yield and/or quality of crops produced by the plant.

After having cultured the transformants in the presence of Hygromycin, 20 different lines for molecular and biochemical analysis were selected. The presence of the gene from $T_o$ to $T_4$ generations has been proved by PCR, Southern, Northern and Western analysis. Out of the 20 lines at $T_o$, 17 lines were positive for Hygromycin and 11 lines were positive for MnSOD. The 11 lines that were positive for MnSOD and Hygromycin were selected for biochemical and physiological experimentation. The product of native engineered protein has been assayed and immunolocalised to the Chloroplast. Out of the 144 lines from the $T_1$ generation 14 lines are selected for further analysis to carry out physiological experiments for SOD and Oxidative stress.

These include herbicide resistance, high and low temperatures, Ultra Violet light and drought.

The Godawari 8 and Salween 2 rice varieties of the *Indica* rice reveal higher levels of SOD activity and SOD protein when compared to controls. Conductance measurement reflective of oxygen radical scavenging ability shows greater protection in case of transgenic Goadawari and Salween _d_ (Fv/Fm) (change in chlorophyll fluorescence) representing chloroplast environment which in turn reveals a healthier chloroplast in the case of the transgenic Godawari 8 even under Methylviologen treatment, when compared with the control plants. The Catalase levels have been up-regulated in the transgenic line, Godawari which displayed a higher level of Godawari activity. A preliminary study of the cell viability under stress demonstrated the fact that the transgenic Godawari performed better than the controls.

To ameliorate the damage caused by hydroxyl radical formed from superoxide radical and hydrogen peroxide, organisms have evolved mechanisms to control the concentration of the two reactants. Superoxide dismutase (SOD) is a group of isozymes functioning as superoxide radical scavenger in the living organisms. Thus they protect the plant cells from superoxide radicals. The reaction of SOD is as follows:

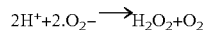

$$2H^+ + 2.O_2^- \longrightarrow H_2O_2 + O_2$$

The produced hydrogen peroxide is then detoxified by catalase or peroxidase.

In eukaryotes, the MnSOD is a nuclear encoded protein that scavenges superoxide radicals in the mitochondrial matrix. By targeting this enzyme to the chloroplast where the generation of superoxide radicals is high during stress conditions, the capacity to scavenge any radical that may be produced can be increased. In an attempt to improve stress tolerance of rice plants, an expression vector containing a *Nicotiana plumbaginicolia* MnSOD cDNA driven by a cauliflower mosaic virus 35S promoter was transferred into the TP309 *Japonica* rice callus by particle gun bombardment (using particle accelerator biolistic PDS100/He). To target this enzyme into the chloroplast, the mature MnSOD coding sequence was fused to a chloroplast transit peptide from Pea ribulose-1-5-biophosphate carboxylase gene.

Transgenic rice *Oryza saiva* plants have been generated that overproduce the *Nicotiana plumbaginicolia* L. MnSOD. This was followed by selection and regeneration of plants. After culture in the presence of hygromycin, twenty different lines were selected for molecular and biochemical analysis. Out of twenty lines at $T_0$, seventeen lines were positive for hygromycin and eleven lines were positive for MnSOD. The eleven lines which were positive for MnSOD and hygromycin, were selected for biochemical and physiological experiments. At present 144 lines from the $T_1$ generation exist and fourteen lines are selected for further work on physiological experiments on SOD and oxidative stress. The present invention proves the presence of the gene from $T_0$ to $T_3$ generations by PCR, Southern, Northern and Western analysis.

Growth characteristics and in vitro oxidative stress tolerance of transgenic lines were evaluated. The transgenic lines Godawari 8 and Salween 2 showed higher levels of SOD activity and SOD protein when compared to controls as indicated in FIG. 1a.

Figure 1B:
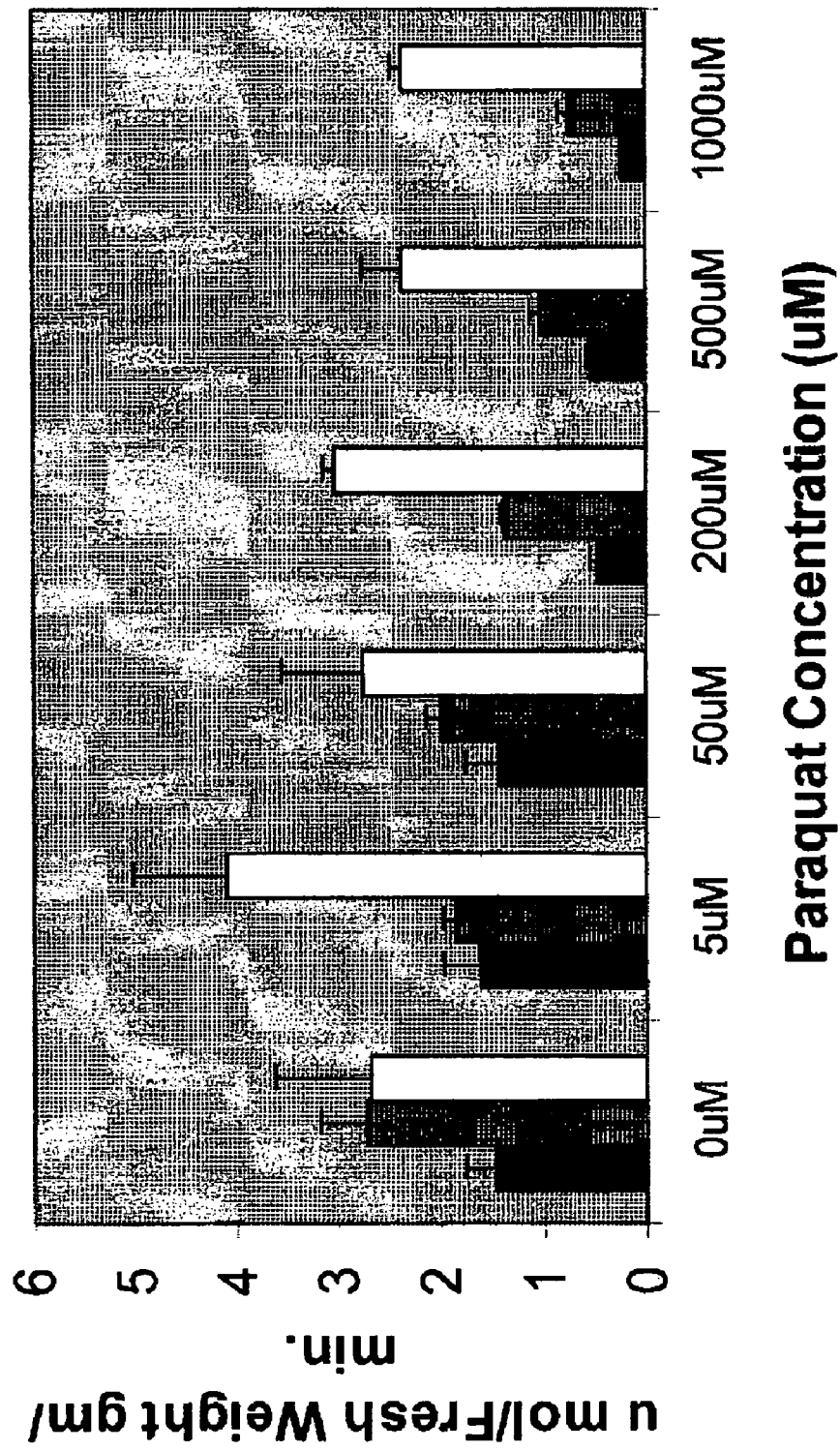
FIG. 1b shows levels of catalase activity in TP309, Salween 2 and Godawari 8.
Figure 1C:
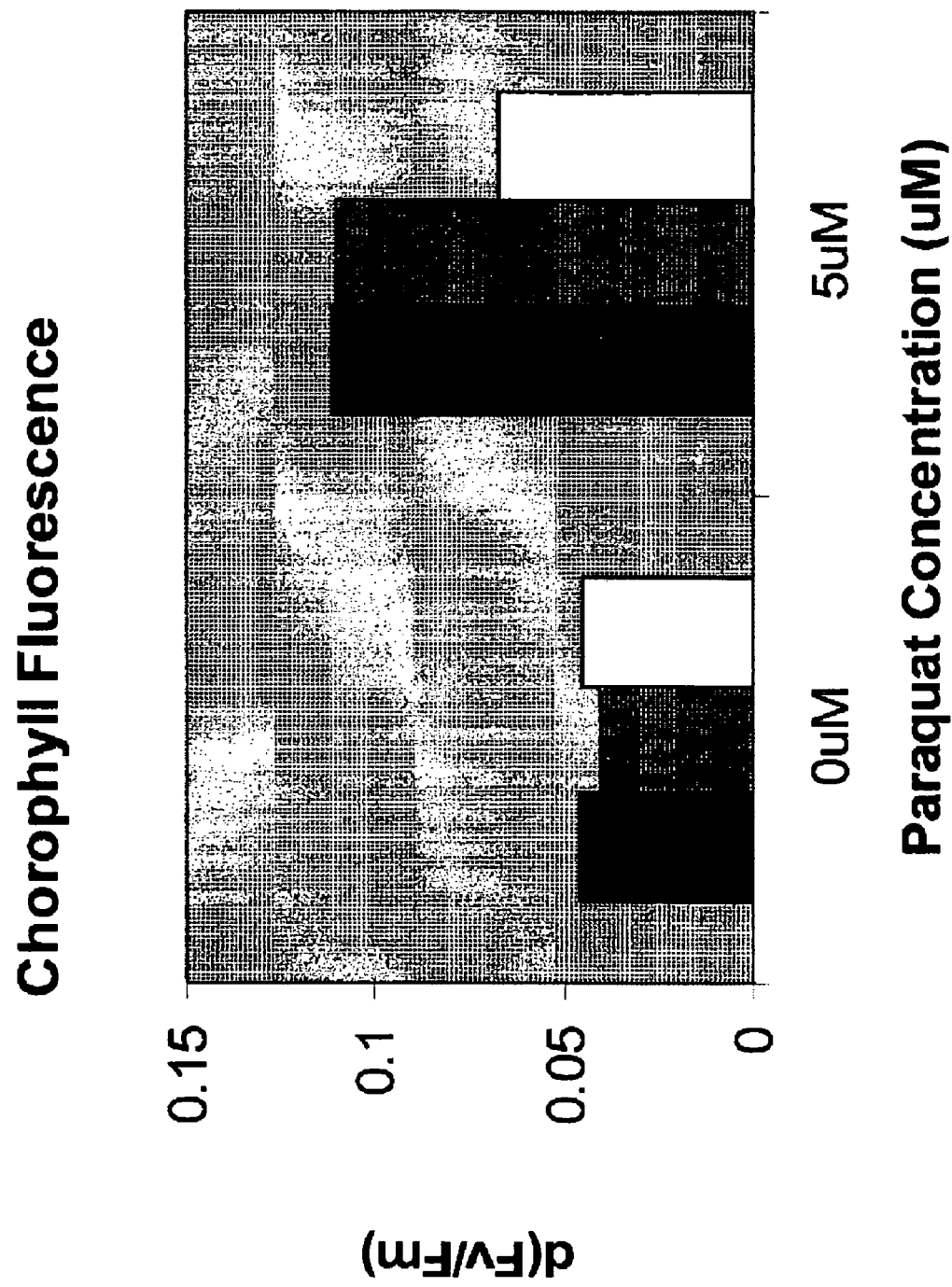
FIG. 1c shows chlorophyll fluorescence in TP309, Salween 2 and Godawari 8.

As shown in FIG. 1a, the transgenic plants showed increased MnSOD activity as compared to non-transgenic plants in the presence of increased methylviologen concentration. In addition, catalase levels were upregulated in the transgenic lines Godawari 8 that had higher level of SOD activity (FIG. 1b). Conductance measurement reflective of oxygen radical scavenging abilities shows greater protection in case of transgenic Godawari and Salween, representing chloroplast environment shows healthier chloroplast in case of the transgenic Godawari 8 even under Methylviologen (Paraquat) treatment, when compared with control plants (FIG. 1c). The presence of transgenic MnSOD activities had enhanced tolerance to Methylviologen and had increased growth rates.

Figure 2A:
FIG. 2a shows cell viability in stress environment after 8 and 12 hours.
Figure 2B:
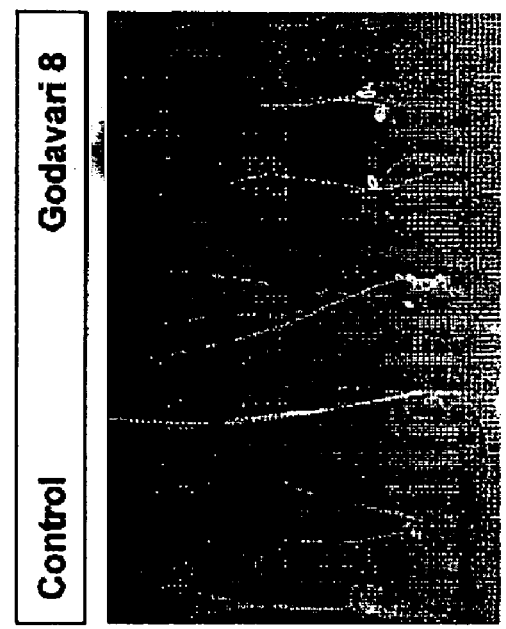
FIG. 2b shows root length growth assay under stress conditions.
Figure 2B:
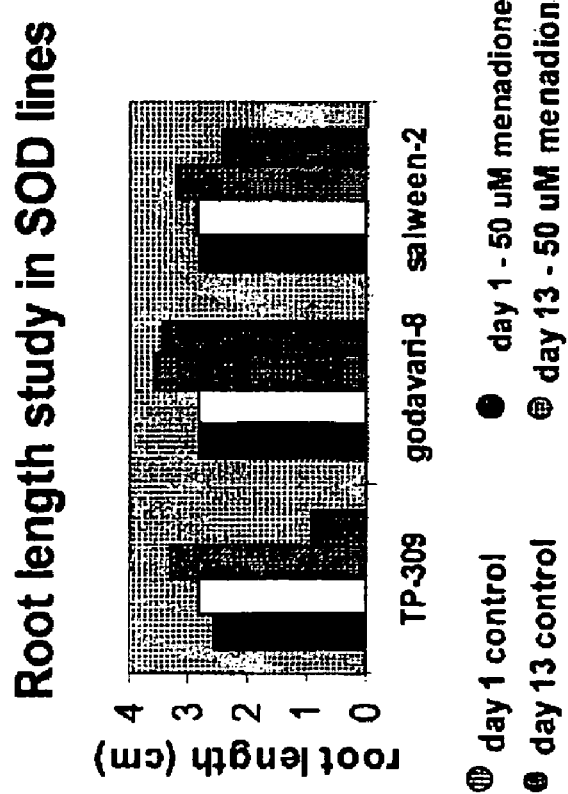

Preliminary studies looking at cell viability and Root length growth assay under stress revealed that the Transgenic Godawari 8 performed better than the controls. (FIGS. 2a and 2b).

Figure 3C:
FIG. 3c shows immunolocalization studies of the native engineered protein in chloroplast.
Figure 3A:
FIG. 3a shows a transgenic plant.
Figure 3A:
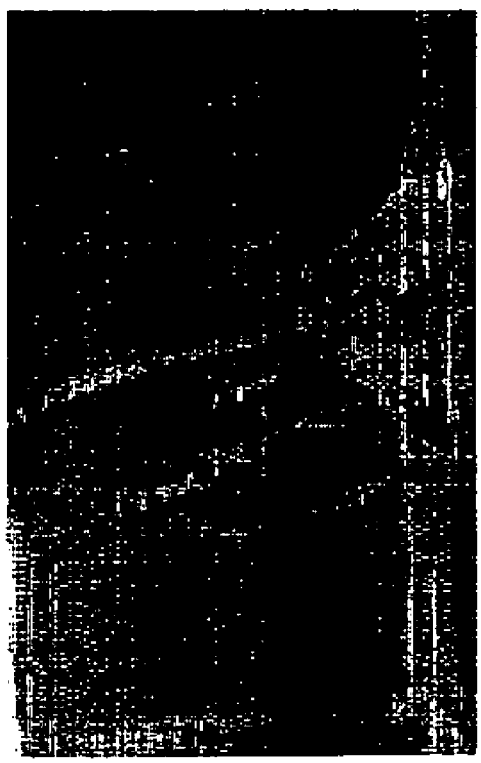
Figure 3B:
FIG. 3b shows a Northern blot analysis of the transgenic plant

The production of the native engineered protein has been assayed for expression by Northern blot analysis and is expressed in chloroplast as shown by immunolocalization studies (FIGS. 3a and 3b).

The transgenic plants also exhibited considerable tolerance against oxidative damage induced by methyl viologen. The degree of abiotic stress tolerance of transgenic T(1) and T(2) plants was found to be significantly greater than that of wild-type rice plants as also measured by survival rate, chlorophyll fluorescence value, and radical elongation. The catalase activity was also highly induced in the transgenic tomato plants.

The level of $H_2O_2$ in the transgenic plants was lower than that in the wild-type plants under either normal or cold conditions. Results from the current study suggest that heterologous MnSOD expression in transgenic rice plants may induce several oxidative-stress responsive genes to protect from drought (abiotic) stress.

Procedure
1. Transgenic *Japonica* rice plants were generated by co-transforming 3 week old scutellum callus using particle accelerator Biolistic PDS-1000/He with plasmids, pGV2 and pILTAB222.
2. The plasmid pGV2 carried the MnSOD cDNA cloned down stream of CvMV promoter and the chloroplast targeting peptide followed by the NOS terminator.
3. The pILTAB222 carried the Hygromycin B phosphotransferase downstream of 35S CaMV promoter and followed by the NOS terminator.
4. The presence of the MnSOD gene was proved in the $T_o$ to $T_4$ generations by PCR, Southern, Northern and Western analysis It has been found that as a result of this type of an application, there is an induction of the endogenous MnSOD expression in the chloroplast, where mostly, damaging effects of ROS occur Dietary antioxidants are compounds in the human diet that may act to scavenge reactive oxygen species (ROS)—molecules which damage macromolecules such as DNA, carbohydrates and proteins. They play an important economic role in the processed food industry by increasing shelf life and maintaining the organo-leptic properties, vitamin content and the eye-appeal of foods.

The invention as has been stated supra, provides the means for growing crops in areas where it cannot be grown with reasonable yields on account of stress conditions including herbicide resistance, high and low temperatures, drought and ultra violet light, and, by producing a highly reactive oxygen species in one or more compartments of the plant cells, it can increase the yield and also the crop quality.

The invention, as can be gathered demonstrates the effectiveness of transformation of the plant species which provides for the expression of superoxide dismutase in a cell organelle, namely, the chloroplast. Transgenic plants are thereby generated which display increased tolerance to environmental stress.

Information pertaining to deposit of biological material is as follows:
Godavari 8 and Salween 2
ACCESSION NUMBER FOR THE DEPOSIT: MTCC5364
DATE OF DEPOSIT: 5 Jul. 2007
NAME AND ADDRESS OF DEPOSITORY: INSTITUTE OF MICROBIAL TECHNOLOGY SECTOR 39-A, CHANDIGARH-160 036 INDIA
Deposit Information A deposit of at least 2500 seeds of transgenic indica rice variety designated Godavari 8 has been made with the American Type Culture Collection (ATCC). The date of deposit is Sep. 28, 2010 and the accession number for the deposited seeds of transgenic indica rice variety designated Godavari 8 is Accession No. PTA-11392. A deposit of at least 2500 seeds of transgenic indica rice variety designated Salween 2 has been made with the American Type Culture Collection (ATCC). The date of deposit is Sep. 28, 2010 and the accession number for the deposited seeds of transgenic indica rice variety designated Salween 2 is Accession No. PTA-11391. Additionally, Applicant has or will satisfy all the requirements of 37 C.F.R. §1.801-1.809.

The invention claimed is:
1. A transgenic indica rice variety designated Godavari 8, representative seed of said transgenic indica rice variety having been deposited under Rice/Paddy seeds, Oriza sativa, Godawari-8 with Accession Number PTA-11392.
2. A transgenic indica rice variety designated Salween 2, representative seed of said transgenic indica rice variety having been deposited under Rice/Paddy seeds, Oriza sativa, Salween-2 with Accession Number PTA-11391.

* * * * *